United States Patent [19]

Davis et al.

[11] 4,420,485
[45] Dec. 13, 1983

[54] 1'-[3-(1,2-BENZISOXAZOL-3-YL) PROPLY]SPIRO[BENZOFURAN-2(3H),3' OR 4'-PIPERIDINES OR 3'-PYRROLIDINES]

[75] Inventors: Larry Davis, Sergeantsville; Frank A. Pierrat, Somerset, both of N.J.

[73] Assignee: Hoechst-Roussel Pharmaceuticals Inc., Somerville, N.J.

[21] Appl. No.: 424,379

[22] Filed: Sep. 29, 1982

[51] Int. Cl.³ ............... A61K 31/445; A61K 31/42; C07D 413/14
[52] U.S. Cl. ............................ 424/267; 424/274; 546/17; 548/408
[58] Field of Search ............... 548/409; 546/17; 424/267, 274

[56] References Cited

U.S. PATENT DOCUMENTS

| | | | |
|---|---|---|---|
| 3,629,239 | 12/1971 | Kitahonoki et al. | 260/239 E |
| 3,732,306 | 5/1973 | Gutman et al. | 564/254 |
| 3,951,999 | 4/1976 | Saunders et al. | 548/241 |
| 3,960,951 | 6/1976 | Gutman | 564/254 |
| 4,007,227 | 2/1977 | Baker et al. | 564/254 |
| 4,128,580 | 12/1978 | Matsumoto et al. | 564/254 |
| 4,166,119 | 8/1979 | Effland et al. | 424/267 |
| 4,166,120 | 8/1979 | Effland et al. | 424/267 |
| 4,192,896 | 10/1979 | Uno et al. | 548/241 |
| 4,235,914 | 11/1980 | Sasajima et al. | 544/401 |

FOREIGN PATENT DOCUMENTS

| | | | |
|---|---|---|---|
| 40639 | 12/1981 | European Pat. Off. | 546/20 |
| 684398 | 3/1965 | Italy | 564/254 |
| 49-70963 | 7/1974 | Japan | 548/241 |
| 51-36666 | 11/1976 | Japan | 548/241 |
| 53-77057 | 7/1978 | Japan | 548/241 |

OTHER PUBLICATIONS

Uno et al., "Chem Pharm Bull" (Japan) vol. 24, No. 4, pp. 632–643.
Noller "Textbook of Organic Chemistry" 3rd Edition (1966) (Saunders) p. 169.
Katritzky "Advances in Heterocyclic Chemistry" vol. 8, pp. 283–286 (1967).
Chemical Abstracts, vol. 87, (1977) Item 39459C, abstracting Japan Kokai 76, 136,666, Nov. 26, 1979.
Janssen "Internationa J. Neuropharmacology" (1962) vol. 1, pp. 145–148.
U.S. Patent Application Ser. No. 06/257,698, filed Apr. 27, 1981.
U.S. Patent Application Ser. No. 06/366,247, filed Apr. 9, 1982.

*Primary Examiner*—Robert T. Bond
*Attorney, Agent, or Firm*—Jerome Rosenstock

[57] ABSTRACT

This invention relates to 1'-[3-(1,2-benzisoxazol-3-yl)propyl]spiro[benzofuran-2(3H),3' or 4'-piperidines or 3'-pyrrolidines] of the formula:

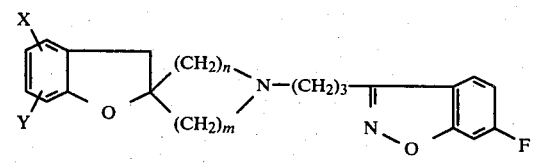

where X and Y are the same or different and are hydrogen, halogen, lower alkoxy, lower alkyl, nitro, hydroxyl and CF₃; and n is an integer of 1 or 2; m is an integer of 2 or 3; and the sum of m and n is 3 or 4; and the pharmaceutically acceptable acid addition salts thereof. These compounds are useful as antihypertensive agents.

37 Claims, No Drawings

1'-[3-(1,2-BENZISOXAZOL-3-YL)PROPLY]SPIRO[BENZOFURAN-2(3H),3' OR 4'-PIPERIDINES OR 3'-PYRROLIDINES]

To the best of our knowledge the compounds of the present invention have not heretofore been described or suggested.

The compounds of the present invention have the general formula:

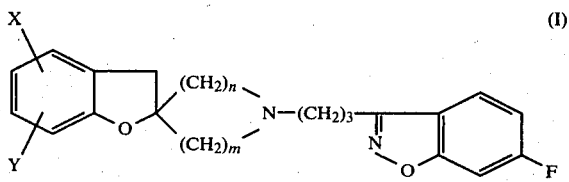

where X and Y are the same or different and are hydrogen, halogen, lower alkoxy, lower alkyl, nitro, hydroxyl and $CF_3$; and n is an integer of 1 or 2; m is an integer of 2 or 3; and the sum of m and n is 3 or 4; and the pharmaceutically acceptable acid addition salts thereof.

Particularly preferred compounds of the invention have the formula

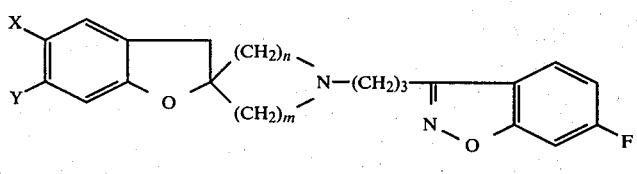

where X and Y are the same or different and are H and halogen.

In the above definitions and as used hereinafter, the term "lower" means the group it is describing contains 1 to 6 carbon atoms. The term "alkyl" refers to a straight or branched chain hydrocarbon containing no unsaturation. The term "alkoxy" refers to a monovalent substituent which consists of an alkyl group linked through an ether oxygen having its free valence bond from the ether oxygen. The term "halogen" refers to a member of the family consisting of fluorine, chlorine, bromine and iodine.

The compounds of the present invention are prepared in the following manner. The substituents X and Y and the integers m and n are as defined above unless indicated otherwise.

A. A substituted piperidine or pyrrolidine of the formula

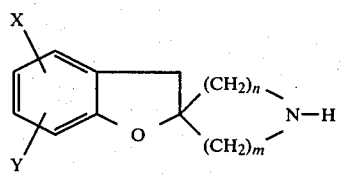

is selected. Compound III is typically prepared by first preparing a Grignard reagent or an organometallic, e.g. organolithium compound, from a halo substituted benzyl halide of the formula

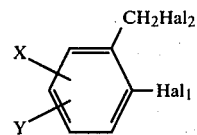

where $Hal_1$ and $Hal_2$ are halogens and preferably $Hal_1$ is fluorine. The resultant Grignard reagent or organometallic is then reacted with a ketone having the formula

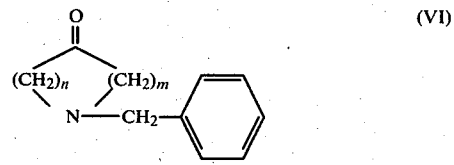

using conventional techniques and conditions to form a piperidinol or pyrrolidinol having the formula

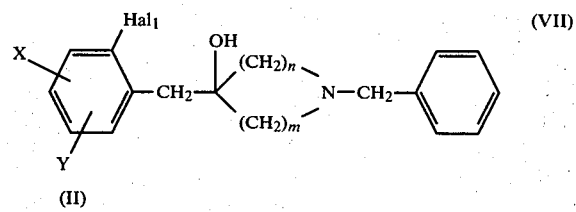

The compound (VII) is then cyclized (condensed) in a conventional manner by heating in a solvent, such as DMF, in the presence of a strong base, e.g. NaH, etc., at a temperature typically ranging from 70° to 100° C. for 2 to 6 hours to form a compound having the formula

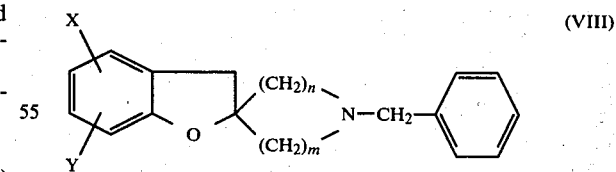

Compound VIII is then subjected to conventional catalytic debenzylation employing hydrogen and a catalyst, e.g. palladium-on-carbon, Raney Nickel, etc. to form compound III.

Where X and Y in compound III are hydrogen, compound III can be halogenated by treatment in a conventional manner with a halogenating agent such as N-bromosuccinimide and/or N-chlorosuccinimide to form compound III where X and/or Y are Br or Cl or both.

B. A substituted benzisoxazole of the formula

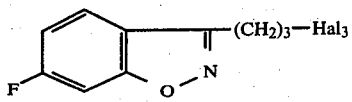

where Hal₃ is a halogen, is selected. Compound IX is typically prepared by cyclizing (condensing) a hydroxybutyrophenone-o-acetyl oxime of the formula

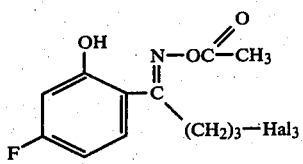

by heating at 25° to 50° C. for 1 to 10 hours in the presence of a base, e.g. K₂CO₃, etc. in a solvent such as 2-butanol.

C. Compound I of the invention is prepared by reacting compound III with compound IX under conventional substitution reaction conditions, typically in the presence of a polar solvent, e.g. dimethylformamide (DMF), a base, such as for example K₂CO₃, at a temperature of 50° to 100° C. for 2 to 5 hours. Where Hal₃ is Cl or Br, a catalytic amount of KI may be added to catalyze the substitution reaction.

The compounds of the invention are useful as antihypertensive agents due to their ability to lower the blood pressure in mammals. The activity of the compound is demonstrated in the spontaneous hypertensive rat screen.

Candidate drugs are prepared in distilled water and administered orally in volumes of 10 ml/kg. Spontaneous hypertensive rats with systolic blood pressures of at least 150 mm Hg are divided into groups of 4 animals/dose. Each animal is used as his own control. The change in systolic blood pressure is expressed in mm Hg. The rats are prepared for recording of blood pressures in the following manner. Each animal is placed in an individual triangular cage and then placed into an environmental chamber kept at 32±0.05° C. A tubular inflatable cuff is placed around the base of the tail and a sensor bulb for detecting indirect tail pulse is then taped to its ventral surface. The sensor bulb is attached to a pneumatic pulse transducer and amplified and displayed on a Gould polygraph. The cuff is inflated to approximately 300 mm Hg. As the pressure in the cuff is slowly released, the systolic pressure is detected and subsequently recorded on the polygraph chart paper.

Compounds which are evaluated for the first time for hypotensive activity are evaluated at 50 mg/kg, orally (p.o.) for three days. After the control blood pressures are taken on day one the animals receive the test drug once daily for three days. Two hours postdrug, on day three, blood pressure is again determined.

The antihypertensive (hypotensive) activity of some of the compounds expressed in decrease in blood pressure (mm Hg) is given in Table I.

TABLE I

| Compound | Dose in mg/kg of body weight (p.o.) | Decrease in Blood Pressure (mm Hg) |
|---|---|---|
| 2,3-dihydro-1'-[3-(6-fluoro-1,2-benzisoxazol-3-yl)propyl]-spiro[benzofuran-2(3H),4'-piperidine] hydrochloride | 50 | 39 |
| 5-bromo-2,3-dihydro-1'-[3-(6-fluoro-1,2-benzisoxazol-3-yl)propyl]-spiro[benzofuran-2(3H),4'-piperidine]hydrochloride | 50 | 32 |
| 5-chloro-2,3-dihydro-1'-[3-(6-fluoro-1,2-benzisoxazol-3-yl)propyl]-spiro[benzofuran-2(3H),4'-piperidine]hydrochloride | 50 | 31 |
| 7-chloro-2,3-dihydro-1'-[3-(6-fluoro-1,2-benzisoxazol-3-yl)-propyl]-spiro[benzofuran-2(3H),4'-piperidine]hydrochloride | 50 | 42 |

The compounds of the invention compare favorably with the well-known drug α-methyl dopa which, in a similar test gave hypotensive activity of −40 mm Hg when administered at 50 mg/kg PO for five days.

The hypotensive relief is achieved when the compounds of the invention are administered to a subject requiring such treatment at an effective oral, parenteral or intravenous dose of from 1.0 to 25 mg/kg of body weight per day. A preferred effective dose within this range is from about 1 to 10 mg/kg of body weight per day. A particularly preferred effective amount is about 5 mg/kg of body weight per day. It is to be understood, however, that for any particular subject, specific dosage regimens should be adjusted according to the individual need. It is further to be understood that the dosages set forth herein are examples only and that they do not, to any extent, limit the scope of practice of the invention.

Effective amount of the compounds of the present invention may be administered to a subject by one of various methods, for example, orally as in capsules or tablets, parenterally in the form of sterile solutions. The compounds of the invention, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphonic, perchloric acids and the like as well as organic acids such as tartaric, citric, acetic, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the active ingredient, but may be varied depending upon the particular form and may conveniently be between 4% to about 7% of the weight of the unit. The amount of the compound present in such compositions is such that a suitable dosage will be obtained. Preferred compositions and preparations according to the present invention are prepared so that an oral dosage unit form contains between 5.0–300 milligrams of the 1'-[3-(1,2-benzisoxazol-3-yl)-propyl]spiro[benzofuran-2(3H),3' or 4'-piperidines or 3'pyrrolidines] of the invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to material of the above type, a liquid carrier such as a fatty oil. Other dosage unit forms may contain other various materials which modify the physical form of the dosage unit, for example, as coatings. Thus, tablets, or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% 1'-[3-(1,2-benzisoxazol-3-yl)propyl]spiro[benzofuran-2(3H),3' or 4'-piperidines or 3'pyrrolidines] of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of 1'-[3-(1,2-benzisoxazol-3-yl)propyl]spiro[benzofuran-2(3H),3' or 4'-piperidines or 3'-pyrrolidines] of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade.

EXAMPLE 1 a. 1-Benzyl-4-(o-fluorobenzyl)-4-piperidinol

To a mixture of magnesium shavings (2.7 g) and anhydrous ether (25 ml) was added a crystal of iodine followed by a few milliliters of o-fluorobenzyl chloride. The reaction was initiated by warming slightly. The remainder of the o-fluorobenzyl chloride (14.5 g, 0.1 mole) in anhydrous ether (75 ml) was added dropwise at a rate to maintain reflux. After the addition was completed (about 45 minutes), the reaction mixture was stirred at reflux for 15 minutes. Ether (50 ml) was added and a solution of N-benzyl-4-piperidone (18.93 g, 0.1 mole) in ether (75 ml) was added slowly dropwise with vigorous mechanical stirring. The resulting suspension was stirred at room temperature for 1–2 hour, then filtered. The filter cake was washed thoroughly with ether, then hydrolyzed by stirring with an ammonium chloride solution. The aqueous mixture was extracted with ether, the ether solution dried with saturated sodium chloride and MgSO$_4$, and the ether removed to give 23.7 g (79%) of oil. The oil was treated with ethereal-HCl to form 1-benzyl-4-(o-fluorobenzyl)-4-piperidinol hydrochloride, m.p. 210°–211° C.

Analysis: Calculated for C$_{19}$H$_{22}$FNO.HCl: 67.94%C, 6.92%H, 4.17N, 5.66%F. Found: 67.93%C, 6.94%H, 4.09%N, 5.74%F.

b. 2,3-Dihydro-1'-benzyl-spiro[benzofuran-2(3H),4'-piperidine]hydrochloride

To a stirred suspension of 50% NaH (98%) (1.4 g) in dry dimethylformamide (DMF) (50 ml) and benzene (10 ml), under nitrogen, was added a solution of 1-benzyl-4-(o-fluorobenzyl)-4-piperidinol (6.9 g, 0.023 mole) of Example 1a, in DMF (25 ml) and benzene (10 ml). The mixture was heated at 110°–120° C., first with an air condenser to allow evaporation of the benzene, for 5 hours. After cooling to room temperature the mixture was poured over ice, water added, and extracted with ether. The ether phase was washed with water, saturated sodium chloride and dried over magnesium sulfate. Removal of the ether afforded 2.5 g (40%) of an oil that solidified to a solid, m.p. 69°–71° C. Recrystallization from methanol gave a solid with the same melting point. The aqueous phase can be again extracted with ethyl acetate to give additional product. Treatment of a solution of the free base (2.5 g) in ether with ethereal-HCl gave 2 g of a solid. Recrystallization from isopropanol gave 2,3-dihydro-1'-benzyl-spiro[benzofuran-2(3H),4'-piperidine]hydrochloride, m.p. 246°–247° C. (1.5 g).

Analysis: Calculated for C$_{19}$H$_{21}$NO.HCl: 72.24%C, 7.03%H, 4.44%N. Found: 71.92%C, 7.06%H, 4.34%N.

c. 2,3-Dihydro-spiro[benzofuran-2(3H),4'-piperidine]

Debenzylation of 2,3-dihydro-1'-benzyl-spiro[benzofuran-2(3H),4'-piperidine] of Example 1b (5.3 g, 0.019 mole) in isopropanol (250 ml) was accomplished by hydrogenation with a Paar shaker (50 psi, 65°–70° C.) and 10% Pd/C catalyst (1 g). After consumption of the theoretical amount of hydrogen (about 5 hours), the solution was cooled to room temperature, the catalyst removed by filtration, and the solvent removed to give a colorless oil which solidified to a solid, 3.4 g (95%). The solid was dissolved in benzene-ether, filtered through Celite, and the solvent removed to give a solid which was triturated with ether to give 2.1 g (58%) of 2,3-dihydro-spiro[benzofuran-2(3H),4'-piperidine], m.p. 56°–58.5° C.

Analysis: Calculated for C$_{12}$H$_{15}$NO: 76.14%C, 8.00%H, 7.40%N. Found: 76.05%C, 8.08%H, 7.27%N.

d. 3-(3-Chloropropyl)-6-fluoro-1,2-benzisoxazole

To 20 ml dry DMF, was added E-γ-chloro-4-fluoro-2-hydroxybutyrophenone-o-acetyl oxime (6.5 g, 0.024 mole) and K$_2$CO$_3$ (4.14 g, 0.03 mole). After stirring at ambient temperature for five hours, the mixture was poured into 500 ml water, stirred for five minutes, then extracted with ether/ethyl acetate. The organic layer was washed twice with water, then dried (saturated NaCl solution, anhydrous MgSO$_4$). After filtering, the solvents were evaporated to an oil, which was Kugelrohr distilled to an oil of 3-(3-chloropropyl)-6-fluoro-1,2-benzisoxazole, 4.0 g (80%), b.p. 130° C./0.5 mm.

Analysis: Calculated for C$_{10}$H$_9$ClFNO: 56.22%C, 4.25%H, 6.56%N. Found: 56.21%C, 4.25%H, 6.52%N.

e.

2,3-Dihydro-1'-[3-(6-fluoro-1,2-benzisoxazol-3-yl)propyl]-spiro[benzofuran-2(3H),4'-piperidine]hydrochloride To 30 ml dry DMF was added 2,3-dihydro-spiro[benzofuran-2,4'-piperidine] of Example 1c (3.0 g, 0.016 mole), 3-(3-chloropropyl)-6-fluoro-1,2-benzisoxazole of Example 1d (4.2 g, 0.02 mole), K$_2$CO$_3$ (10.0 g, 0.07 mole), and KI (0.1 g). After stirring at 90° C. for one and one-half hours, the mixture was evaporated to an oil, stirred with 100 ml water for five minutes, then extracted with ether. The ether solution was washed twice with water, then dried (saturated NaCl, anhydrous MgSO$_4$). After filtering, the ether solution was acidified to pH 1 with ethereal-HCl, and the resultant precipitate collected and dried at 60° C. for three hours under vacuum to yield 5.0 g of material, m.p. 100° C. This material was recrystallized twice from 10:1:5:ethyl acetate/methanol/ether to yield 2.5 g (50%) of 2,3-dihydro-1'-[3-(6-fluoro-1,2-benzisoxazol-3-yl)propyl]-spiro[benzofuran-2(3H),4'-piperidine]hydrochloride, m.p. d @ 245° C.

Analysis: Calculated for C$_{22}$H$_{23}$FN$_2$O$_2$.HCl: 65.58%C, 6.00%H, 6.95%N. Found: 65.21%, 5.91%H, 6.85%N.

EXAMPLE 2 a.

5-Bromo-2,3-dihydro-sprio[benzofuran-2(3H),4'-piperidine]hydrochloride

In 700 ml methanol was added 40.00 g (0.177 mol) 2,3-dihydro-spiro[benzofuran-2(3H),4'-piperidine]hydrochloride of Example 1c and the resultant solution was cooled in ice to 5° C. To it with stirring was added at once 30.0 g (0.169 mol, 0.95 eq) N-bromosuccinimide (NBS). The solution was warmed to ambient temperature during which time the reaction was completed. The solvent was evaporated to a solid. The solid was partitioned between dichloromethane and saturated sodium bicarbonate solution. The dichloromethane was separated, ashed with saturated salt, dried over sodium sulfate and filtered. The hydrochloride salt was formed by adding excess ethereal-HCl to the dichloromethane. The product precipitated out of solution. It was filtered and washed with more dichloromethane then dried at 110° C. under vacuum to yield 34.4 g (64%) of 5-bromo-2,3-dihydro-spiro[benzofuran-2(3H),4'-piperidine]hydrochloride, m.p. 231°-232° C.

Analysis: Calculated for C$_{12}$H$_{14}$BrNO.HCl: 47.3%C, 4.9%H, 4.6%N. Found: 46.88%C, 4.86%H, 4.54%N.

b.

5-Bromo-2,3-dihydro-1'-[3-(6-fluoro-1,2-benzisoxazol-3-yl)propyl]-spiro[benzofuran-2(3H),4'-piperidine]hydrochloride In 50 ml dry MDF were combined 5.0 g (18.7 mmol) 5-bromo-2,3-dihydro-spiro[benzofuran-2(3H),4'-piperidine] of Example 2a, 6.24 g (1.25 eq, 80% solution in toluene) of 3-(3-chloropropyl)-6-fluoro-1,2-benzisoxazole of Example 1d, 15.0 g (6 eq.) milled anhydrous K$_2$CO$_3$, and 0.1 g (catalytic) KI. The reaction mixture was stirred at 90° C. for 1½ hours, then filtered. The residual salts were dissolved in water; the filtrate evaporated in vacuo to a residue. The residue was partitioned between the aqueous salt solution and ethyl acetate. The ethyl acetate was separated, washed with saturated NaCl, dried over MgSO$_4$, filtered and evaporated to 9.0 g of an oil. The oil was dissolved in 300 ml dry ether, filtered, and made acidic with ethereal-HCL. The precipitate was filtered, dried, and recrystallized twice from 10:1:ethyl acetate/methanol to yield 2.22 g (25%) of 5-bromo-2,3-dihydro-1'-[3-(6-fluoro-1,2-benzisoxazol-3-yl)propyl]-spiro[benzofuran-2(3H),4'-piperidine]hydrochloride, m.p. 247°-250° C. (dec.).

Analysis: Calculated for C$_{22}$H$_{22}$BrFN$_2$O$_2$.HCl: 54.8%C, 4.8%H, 5.8%N. Found: 54.78%C, 4.66%H, 5.87%N.

EXAMPLE 3 a.

5,7-Dichloro-2,3-dihydro-spiro[benzofuran-2(3H),4'-piperidine]hydrochloride

In 500 ml methanol were combined 20.0 g (88.7 mmol) 2,3-dihydro-spiro[benzofuran-2(3H),4'-piperidine]hydrochloride of Example 1c and 11.8 g (1 eq.) N-chlorosuccinimide. The reaction was refluxed 1 hour, cooled to room temperature and 11.8 g (1 equivalent) more N-chlorosuccinimide was added. The reaction mixture was refluxed one more hour, then it was evaporated to an oil. The oil was partitioned between saturated NaHCO$_3$ and ethyl acetate. The ethyl acetate was separated, washed with saturated NaCl, dried over MgSO$_4$, filtered and evaporated to 37.1 g of a solid. The solid was dissolved in 1:1 methanol/ethyl acetate and excess ethereal-HCl added to make the hydrochloride salt. The resulting solution was evaporated to a solid which was recrystallized twice from ethyl acetate/methanol (10:1) to obtain 7.72 g (30%) of 5,7-dichloro-2,3-dihydro-spiro[benzofuran-2(3H),4'-piperidine]hydrochloride, melting point 275°-8° C. (softens).

Analysis: Calculated for C$_{12}$H$_{13}$Cl$_2$NO.HCl: 48.9%C, 4.8%H, 4.8%N. Found: 48.54%C, 4.63%N, 4.6%N.

b.

5,7-Dichloro-2,3-dihydro-1'[3-(6-fluoro-1,2-benzisoxazol-3-yl)propyl]-sprio[benzofuran-2(3H),4'-piperidine]maleate In 55 ml dry DMF were combined 5.50 g (21.3 mmol) 5,7-dichloro-2,3-dihydro-spiro[benzofuran-2(3H),4'-piperidine] of Example 3a, 7.11 g (1.25 eq.) 3-(3-chloropropyl)-6-fluoro-1,2-benzisoxazole of Example 1d, 17.64 g (6 equivalents) milled anhydrous K$_2$CO$_3$, and 50 mg KI catalyst. The mixture was stirred under nitrogen at 90° C. for 2 hours then filtered and evaporated in vacuo to an oil. The oil was partitioned between ethyl acetate and 10% Na$_2$CO$_3$ and the ethyl acetate layer separated, washed with saturated salt, dried over MgSO$_4$, filtered and evaporated in vacuo to an oil. The maleate was formed by dissolving the amine in excess ether and adding excess saturated ethereal maleic acid. The precipitate was filtered and recrystallized from isopropanol to yield 1.80 g (15%) of 5,7-dichloro-2,3-dihydro-1'[3-(6-fluoro-1,2-benzisoxazol-3-yl)propyl]- spiro[benzofuran-2(3H),4'-piperidine]maleate, m.p. 200°–201° C.

Analysis: Calculated for $C_{22}H_{21}Cl_2FN_2O_2 \cdot C_4H_4O_4$: 56.63%C, 4.51%H, 5.08%N. Found: 56.56%C, 4.62%H, 5.17%N.

EXAMPLE 4 a. 1-Benzyl-4-(5-chloro-2-fluorobenzyl)-4-piperidinol hydrochloride

To a suspension of 18.6 g (0.77 mole) of Mg shavings in 75 ml of anhydrous ether stirring under nitrogen was added a crystal of iodine followed by a few milliliters of 5-chloro-2-fluorobenzyl bromide. The reaction was initiated by heating, then 138.8 g (0.62 mole) of the benzyl bromide dissolved in 300 ml of ether was added dropwise at a rate maintaining reflux. Upon completion of the addition, the reaction was stirred and refluxed for 0.5 hours, an additional 1500 ml of ether was added, and 102 g (0.54 mole) of N-benzyl-4-piperidone in 1000 ml of ether was added dropwise with vigorous stirring. The resulting suspension was stirred at room temperature overnight (about 16 hours) was filtered and was washed well with ether. The filter cake was hydrolyzed by stirring in an ice-$NH_4Cl$ solution (350 g $NH_4Cl$ in 3 liters $H_2O$). The aqueous solution was extracted four times with ether (250 ml) and dried over $Na_2SO_4$. The excess solvent was evaporated and the residue disilled at 0.15 mm at 210° C. giving 28.3 g of an oil (15.5% yield). A hydrochloride salt was made by dissolving 1 g of the oil in ether and adding a solution of ethereal-HCl. The precipitate was collected and recrystallized thrice from ethanol/ether (1:1) to give 1-benzyl-4-(5-chloro-2-fluorobenzyl)-4-piperidinol hydrochloride, m.p. 217°–219° C.

Analysis: Calculated for $C_{19}H_{21}ClFNO \cdot HCl$: 61.63%C, 5.99%H, 3.78%N, 19.15%Cl. Found: 61.92%C, 6.01%H, 3.83%N, 19.03%Cl.

b. 1'-Benzyl-5-chloro-2,3-dihydro-spiro[benzofuran-2(3H),4'-piperidine]hydrochloride To a stirring suspension of 4.4 g (0.09 mole) of NaH (50% oil dispersion) in 250 ml of benzene stirring at room temperature under nitrogen was added dropwise a solution of 21.5 g (0.065 mole) of 1-benzyl-4-(5-chloro-2-fluorobenzyl)-4-piperidinol of Example 4a, in 150 ml of benzene. The reaction was brought to reflux then 125 ml of DMF was added. The reaction was refluxed for 4 hours, cooled to room temperature, and 100 ml of $H_2O$ was added dropwise. The reaction was porued into 1 liter of ice-$H_2O$, washed with saturated NaCl solution and dried over $Na_2SO_4$. The solvent was evaporated under reduced pressure and the resultant oil was extracted with boiling hexane. The hexane was removed to give 16.5 g (81%) of an oil which solidified on standing. The hydrochloride salt was made by dissolving 1 g of this oil in ether and adding a solution of ethereal-HCl. The precipitate was collected and recrystallized three times from ethyl acetate/methanol (10:1) to give 1'-benzyl-5-chloro-2,3-dihydro-spiro[benzofuran-2(3H),4'-piperidine]hydrochloride, m.p. 255°–258° C.

Analysis: Calculated for $C_{19}H_{20}ClNO \cdot HCl$: 65.15%C, 6.04%H, 4.00%N, 20.24%Cl. Found: 65.21%C, 6.11%H, 3.98%N, 20.06%Cl.

c. 5-Chloro-2,3-dihydro-spiro[benzofuran-2(3H),4'-piperidine]hydrochloride

A solution of 16.0 g (0.065 mole) of 1'-benzyl-5-chloro-2,3-dihydro-spiro[benzofuran-2(3H),4'-piperidine] of Example 4b, 6.9 g (0.09 mole) of ethyl chloroformate and 500 ml of benzene was stirred and refluxed for 24 hours. The reaction was cooled to room temperature, washed with water, 3 N HCl solution, saturated bicarbonate solution, saturated NaCl solution, dried over $Na_2SO_4$, and the solvent evaporated to give approximately 17 g of an oil. The oil was refluxed for 18 hours in 150 ml of 50% KOH solution and 300 ml of ethanol then cooled to room temperature and the ethanol removed under reduced pressure. The remaining aqueous suspension was extracted with ether. The ether extract was washed with 3 N HCl. The acidic wash was basified with 6 N NaOH, then extracted with ether, and the ether extracts dried over $Na_2SO_4$. The solvent was removed to give 8.9 g (61.5%) of a solid. The hydrochloride salt was made by dissolving 0.5 g of the piperidine in ether and adding a solution of ethereal-HCl. The precipitate was collected and recrystallized from ethanol twice and 1:1 ethanol/ether once to give 5-chloro-2,3-dihydro-spiro[benzofuran-2(3H),4'-piperidine]hydrochloride, m.p. 217°–218° C.

Analysis: Calculated for $C_{12}H_{14}ClNO \cdot HCl$: 55.40%C, 5.81%H, 5.38%N, 27.26%Cl. Found: 55.53%C, 5.84%H, 5.40%N, 27.11%Cl.

d. 5-Chloro-2,3-dihydro-1'-[3-(6-fluoro-1,2-benzisoxazol-3-yl)propyl]-spiro[benzofuran-2(3H),4'-piperidine]hydrochloride In 40 ml dry DMF were combined 3.9 g (17.4 mmol) 5-chloro-2,3-dihydro-spiro[benzofuran-2(3H),4'-piperidine] of Example 4c, 5.82 g (1.25 eq., 80% in toluene) of 3-(3-chloropropyl)-6-fluoro-1,2-benzisoxazole of Example 1d, 14.4 g (6 equivalents)) milled $K_2CO_3$, and 50 mg KI. The reaction was heated at 90° C. under nitrogen with stirring for 2 hours then filtered to remove the carbonate salts. The filtrate was evaporated to an oil and partitioned between an aqueous solution of the residual carbonate salts (from the reaction) and ethyl acetate. The ethyl acetate was separated, washed with saturated NaCl, dried over $MgSO_4$, filtered, and evaporated to an oil. The oil was dissolved in 1:1 methanol/ether and the HCl salt made by adding excess ethereal-HCl. The solvent was evaporated and the residue recrystallized twice from (10:1) ethyl acetate/methanol to yield after drying 3.69 g (48%) of 5-chloro-2,3-dihydro-1'-[3-(6-fluoro-1,2-benzisoxazol-3-yl)propyl]-spiro[benzofuran-2(3H),4'-piperidine]hydrochloride, m.p. 254°–256° C.

Analysis: Calculated for $C_{22}H_{22}ClFN_2O_2 \cdot HCl$: 60.4%C, 5.3%H, 6.4%N. Found: 60.63%C, 5.31%H, 6.40%N.

EXAMPLE 5 a. 5-Bromo-7-chloro-2,3-dihydro-spiro[benzofuran-2(3H),4'-piperidine]hydrochloride In 60 ml of methanol were combined 13.2 g (43.3 mmol) of 5-bromo-2,3-dihydro-spiro[benzofuran-2(3H),4'-piperidine]hydrochloride of Example 2a and 6.37 g (1.1 equivalents) N-chlorosuccinimide. The resultant solution was refluxed for one hour and then evaporated to a gum. The gum was diluted with saturated NaHCO$_3$ and taken up in ethyl acetate. The ethyl acetate was separated, washed with water, saturated aqueous salt solution, dried over MgSO$_4$, filtered and evaporated to yield 14.5 g of a solid. The solid was dissolved in 1:10 methanol/ether and the hydrochloride salt was made by the addition thereto of ethereal-HCl. The resultant mixture was evaporated to a solid which was recrystallized from 10:1 ethyl acetate/methanol to yield 2.0 g of 5-bromo-7-chloro-2,3-dihydro-spiro[benzofuran-2(3H),4'-piperidine]hydrochloride, m.p. 260° C.

b.
5-Bromo-7-chloro-2,3-dihydro-1'-[3-(6-fluoro-1,2-benzisoxazol-3-yl)propyl]-spiro(benzofuran-2(3H),4'-piperidine]hydrochloride In 170 ml dry DMF were combined 16.5 g (54.5 mmol) 5-bromo-7-chloro-2,3-dihydro-spiro[benzofuran-2(3H),4'-piperidine] of Example 5b, 18.20 g of 3-(3-chloropropyl)-6-fluoro-1,2-benzisoxazole of Example 1d, 45.2 g (6 equivalents) milled anhydrous K$_2$CO$_3$, and 0.75 g KI as catalyst. The mixture was stirred at 90° C. for one and one-half hours, after which it was complete. The reaction mixture was filtered. The filtrate was reduced in vacuo to an oil. The carbonate salts were dissolved in water and added to the filtrate residue. The mixture was extracted with ethyl acetate. The ethyl acetate was separated, washed with saturated aqueous salt solution, dried over MgSO$_4$, filtered, and evaporated to a residue. The residue was dissolved in dichloromethane and the HCl salt formed by adding ethereal-HCl. The solvent was evaporated and the solid which was recrystallized thrice from 10:1 ethyl acetate/methanol was then dried in vacuo at 110° C. to yield 10.4 g (37%) of 5-bromo-7-chloro-2,3-dihydro-1'-[3-(6-fluoro-1,2-benzisoxazol-3-yl)propyl]-spiro[benzofuran-2(3H),4'-piperidine]hydrochloride, m.p. 232°-234° C.

Analysis: Calculated for C$_{22}$H$_{21}$BrClFN$_2$O$_2$.HCl: 51.2%C, 4.3%H, 5.4%N. Found: 51.34%C, 4.24%H, 5.43%N.

EXAMPLE 6 a.
7-Chloro-2,3-dihydro-spiro[benzofuran-2(3H),4'-piperidine]hydrochloride

In 100 ml of dry tetrahydrofuran (THF) was added 2.74 g (8.08 mmol) of 5-bromo-7-chloro-2,3-dihydro-spiro[benzofuran-2(3H),4'-piperidine] of Example 5b and the resultant solution was cooled to −60° C. with stirring under nitrogen. Added to the cooled solution was 11.11 ml (3.3 equivalent) of 2.4 M n-butyllithium in hexanes, maintaining the temperature at −60° C. After 5 minutes, the reaction mixture was quenched with 5 ml of water and evaporated in vacuo. The resultant residue was partitioned between water and ether and the ether was separated and washed with saturated aqueous salt solution and dried over MgSO$_4$. The MgSO$_4$ was filtered and the ether was evaporated to leave 2.0 g of an oil. The oil was dissolved in 200 ml of ether and the pH adjusted to 1 with ethereal-HCl. The resulting precipitate was separated and recrystallized from 1:1 isopropanol/ethyl acetate to yield 1.2 g (61%) of 7-chloro-2,3-dihydro-spiro[benzofuran-2(3H),4'-piperidine]hydrochloride which softens at 240° C.

b.
7-Chloro-2,3-dihydro-1'-[3-(6-fluoro-1,2-benzisoxazol-3-yl)propyl]-spiro[benzofuran-2(3H),4'-piperidine]hydrochloride In 200 ml dry DMF were combined 12.3 g (6 equivalents) milled anhydrous K$_2$CO$_3$, 3.86 g (14.8 mmol) 7-chloro-1,2-dihydro-spiro[benzofuran-2(3H),4'-piperidine]hydrochloride of Example 6a, 4.96 g (1.25 equivalent, 80% in toluene) 3-(3-chloropropyl)-6-fluoro-1,2-benzisoxazole of Example 1d, and 0.75 g of KI catalyst. The mixture was heated to 90° C. with stirring for 2 hours. It was then cooled, filtered, and the DMF removed at 80° C. in vacuo. The residual oil was taken up in ether and washed with 10% Na$_2$CO$_3$, water, saturated salt, dried over MgSO$_4$, filtered, and the ether solution adjusted to pH 1 with excess ethereal-HCl. The resulting precipitate was filtered and recrystallized from 10:1 ethyl acetate/methanol to yield 3.10 g (48%) of 7-chloro-2,3-dihydro-1'-[3-(6-fluoro-1,2-benzisoxazol-3-yl)propyl]-spiro[benzofuran-2(3H),4'-piperidine]hydrochloride, m.p. 228°-229° C.

Analysis: Calculated for C$_{22}$H$_{22}$ClFN$_2$O$_2$.HCl: 60.42%C, 5.30%H, 6.41%H. Found: 59.98%C, 5.17%H, 6.52%H.

EXAMPLE 7 a.
R,S-3-(2-fluorophenylmethyl)-1-phenylmethylpiperidin-3-ol

Under nitrogen was added dropwise 50.38 g of 2-fluorobenzyl chloride in ether (125 ml solution) to 9.31 g (1.1 equivalent) of Mg turnings in 10 ml of ether. After addition was complete, the reaction mixture was heated to reflux for ten minutes and then cooled to room temperature. To the mixture was added dropwise 52.68 g (0.279 mole, 0.80 equivalent) of 1-benzyl-3-piperidone. After addition, the resultant biphasic solution was stirred for one hour and quenched with excess saturated NH$_4$Cl. The biphasic solution was filtered through Celite and extracted with ethyl acetate. The ethyl acetate was washed with saturated aqueous salt solution, dried over MgSO$_4$, filtered and evaporated to 88.8 g of an oil of R,S-3-(2-fluorophenylmethyl)-1-phenylmethylpiperidin-3-ol.

b.
2,3-Dihydro-1'-(phenylmethyl)-spiro[benzofuran-2(3H),3'-piperidine]hydrochloride In 500 ml of dry DMF and 24.4 g (2 equivalents) NaH was added 76.1 g (0.255 mol) of R,S-3-(2-fluorophenylmethyl)-1-phenylmethylpiperidine-3-ol of Example 7a in 200 ml dry DMF. The reaction mixture was heated to 110°-120° C. for 2 hours. The excess NaH was neutralized by the addition of 100 ml of ethanol and the resulting solution was evaporated to an oil. The oil was extracted with 10:1 ether/water, filtered and the ether was separated. The ether was washed with water, saturated aqueous salt solution, dried over MgSO$_4$, filtered and evaporated to 62.1 g of an oil. The oil was purified by high pressure liquid chromatography (HPLC) to yield 30.8 g of an oil. The oil was dissolved in ether and adjusted to pH 1 with ethereal-HCl. The resultant precipitate was collected and recrystallized from 1:5 methanol/ethyl acetate to yield 20 g of 2,3-dihydro-1-(phenylmethyl)-spiro[benzofuran-2(3H),3'-piperidine]hydrochloride, m.p. 206°-209° C.

Analysis: Calculated for $C_{19}H_{21}NO\cdot HCl$: 72.2%C, 7.0%H, 4.4%N. Found: 71.34%, 6.52%H, 4.3%N.

c.
2,3-Dihydro-spiro[benzofuran-2(3H),3'-piperidine]hydrochloride

To 5.0 g (15.8 mml) of 2,3-dihydro-1'-(phenylmethyl)-spiro[benzofuran-2(3H),3'-piperidine]hydrochloride of Example 7b in 250 ml of isopropyl alcohol was added 1.0 g of 10% Pd/C catalyst. The resultant mixture was hydrogenated at 50° C. at 51 psi for 3 hours. The mixture was filtered and the filtrate was concentrated to 4.39 g of a residue. The residue was washed with ether and recrystallized from 1:1 ethyl acetate/dichloromethane to yield 1.72 g (48%) of 2,3-dihydro-spiro[benzofuran-2(3H),3'-piperidine]hydrochloride, m.p. 212° C.

Analysis: Calculated for $C_{12}H_{15}NO\cdot HCl$: 63.9%C, 7.1%H, 6.2%N. Found: 63.16%C, 7.18%H, 6.15%N.

d.
(R,S)-2,3-Dihydro-1'-[3-(6-fluoro-1,2-benzisoxazol-3-yl)propyl]-spiro[benzofuran-2(3H),3'-piperidine]hydrochloride In 50 ml dry dimethylformamide (DMF) were combined 5.00 g (22.2 mmol) 2,3-dihydro-spiro[benzofuran-2(3H),3'-piperidine]hydrochloride of Example 1c, 7.41 g (1.25 equivalents) 3-(3-chloropropyl)-6-fluoro-1,2-benzisoxazole of Example 1d, 18.4 g (6 equivalents) milled anhydrous potassium carbonate, and a catalytic amount (0.5 g) potassium iodide. The mixture was stirred under nitrogen at 90° C. for three and one-half hours, then cooled and filtered. The DMF was evaporated in vacuo to an oil which was partitioned between 10% $K_2CO_3$ and ether. The ether was separated, washed with water, saturated aqueous alt solution, dried over $MgSO_4$, filtered, and passed through a column of 40 g alumina in ether. The product-containing fractions were combined and adjusted to pH 1 with ethereal-HCl. The resultant precipitate was collected and recrystallized from 1:1 dichloromethane/ethyl acetate to yield 3.36 g (38%) of (R,S)-dihydro-1'-[3-(6-fluoro-1,2-benzisoxazol-3-yl)propyl]-spiro[benzofuran-2(3H),3'-piperidine]hydrochloride, m.p. 257°-259° C.

Analysis: Calculated for $C_{22}H_{23}FN_2O_2\cdot HCl$: 65.58%C, 6.00%H, 6.95%N. Found: 65.50%C, 5.89%H, 6.99%N.

EXAMPLE 8 a.
5-Chloro-2,3-dihydro-spiro[benzofuran-2(3H),3'-piperidine]hydrochloride In 100 ml of methanol were combined 5.00 g (22.2 mmol) of 2,3-dihydro-spiro[benzofuran-2(3H),3'-piperidine]hydrochloride of Example 7c and 2.96 g (1 equivalent) of N-chlorosuccinimide. The resultant mixture was stirred and heated to reflux. After about 0.5 hour, the solvent was reduced in vacuo to form a residue which was partitioned between ether/10% $Na_2CO_3$. The ether was washed with saturated aqueous salt solution, dried over $MgSO_4$, filtered and adjusted to pH 1 with excess ethereal-HCl. The resultant precipitate was collected and washed with 1:1 dichloromethane/ethyl acetate and then recrystallized from 1:5 methanol/ethyl acetate to yield 3.25 g (56%) of 5-chloro-2,3-dihydro-spiro[benzofuran-2(3H),3'-piperidine]hydrochloride, m.p. 235°-237° C.

Analysis: Calculated for $C_{12}H_{14}ClNO\cdot HCl$: 55.4%C, 5.8%H, 5.4%N. Found: 55.25%C, 5 9%H, 5.43%N.

b.
5-Chloro-2,3-dihydro-1'-[3-(6-fluoro-1,2-benzisoxazol-3-yl)propyl]-spiro[benzofuran-2(3H),3'-piperidine]maleate In 40 ml dry DMF were combined 3.18 g (12.2 mmol) 5-chloro-2,3-dihydro-spiro[benzofuran-2(3H),3'-piperidine]hydrochloride of Example 8a, 4.08 g (1.25 equivalents) of an 80% solution of 3-(3-chloropropyl)-6-fluoro-1,2-benzisoxazole of Example 1d in toluene, 10.1 g (6 equivalents) milled anhydrous $K_2CO_3$, and 0.1 g of KI catalyst. The mixture was stirred under nitrogen at 90° C. for 2 hours then filtered. The DMF was removed by evaporation under vacuum. The residual oil was partitioned between ether and 10% $Na_2CO_3$ solution. The ether was separated, washed with saturated salt solution, dried over $MgSO_4$, filtered, and adjusted to pH 1 with ethereal maleic acid. The resultant precipitate was collected and recrystallized from isopropyl alcohol to obtain 1.89 g (35%) of 5-chloro-2,3-dihydro-1'-[3-(6-fluoro-1,2-benzisoxazol-3-yl)propyl]-spiro[benzofuran-2(3H),3'-piperidine]maleate, m.p. 172°-173° C.

Analysis: Calculated for $C_{22}H_{22}ClFN_2O_2\cdot C_4H_4O_4$: 60.41%C, 5.07%H, 5.42%N. Found: 60.45%C, 5.17%H, 5.58%N.

EXAMPLE 9 a.
(R,S)-5-Bromo-2,3-dihydro-spiro[benzofuran-2(3H),3'-piperidine]hydrochloride In 10 ml of methanol was added 0.5 g (2.65 mmol) of 2,3-dihydro-spiro[benzofuran-2(3H),3'-piperidine]hydrochloride and the resultant solution was cooled in ice. To this was added 0.47 g (1 equivalent) of N-bromosuccinimide. After five minutes, the reaction mixture was evaporated in vacuo and partitioned between 1:1 dichloromethane/$NaHCO_3$ solution. The dichloromethane was washed with water, saturated aqueous salt solution, dried over $MgSO_4$ and ethereal HCl was added thereto. The resultant acidic solution was diluted with ethyl acetate and concentrated to effect crystallization to yield 0.52 g (64%) of (R,S)-5-bromo-2,3-dihydro-spiro[benzofuran-2(3H),3'-piperidine]hydrochloride, m.p. 203°-205° C. dec.

Analysis: Calculated for $C_{12}H_{14}BrNO\cdot HCl$: 47.32%C, 4.9%H, 4.6%N. Found: 46.80%C, 4.79%H, 4.53%N.

b.
5-Bromo-7-chloro-2,3-dihydro-spiro[benzofuran-2(3H),3'-piperidine]hydrochloride In 150 ml of methanol were combined 9.47 g (31.088 mmol.) of 5-bromo-2,3-dihydro-spiro[benzofuran-2(3H),3'-piperidine]hydrochloride of Example 9a and 4.57 g (1.10 equivalent) of N-chlorosuccinimide. The resultant solution was refluxed for 1.5 hours whereupon the solution was evaporated to a residue. The residue was partitioned between 1:1 ether/10% $Na_2CO_3$ to generate the free amine. The ether was separated, washed twice with 100 ml. of 10% $Na_2CO_3$, washed with water and then with saturated aqueous salt solution, dried over $MgSO_4$ and filtered. The ether solution was adjusted to pH 1 with ethereal-HCl, and the resultant precipitate was collected and recrystallized from 5:1 ethyl acetate/methanol to yield 4.65 g (44%) of 5-bromo-7-chloro-2,3-dihydro-spiro[benzofuran-2(3H),3'-piperidine]hydrochloride, m.p. 210°-213° C.

c.

7-Chloro-2,3-dihydro-spiro[benzofuran-2(3H),3'-piperidine]hydrochloride

In 250 ml of tetrahydrofuran (THF) was added 4.65 g (13.714 mmol) of 5-bromo-7-chloro-2,3-dihydro-spiro[benzofuran-2(3H),3'-piperidine]hydrochloride of Example 7b. The resultant mixture was cooled to −60° C. to −70° C. under nitrogen and to this was added with stirring 20 ml of n-butyllithium in hexanes (2.4 M, 3.5 equivalents) at a rate which kept the temperature at −60° C. After 30 minutes, water was added to the reaction mixture and the temperature thereof was brought to room temperature. The solvent thereof was reduced in vacuo to yield a residue which, in turn, was partitioned between 1:1 ether/10% Na$_2$CO$_3$. The ether was separated and washed with 100 ml. of 10% Na$_2$CO$_3$, water and saturated brine and then dried over MgSO$_4$, filtered then adjusted to pH 1 with ethereal-HCl. The resultant precipitate was collected to yield 3.12 g (87%) of 7-chloro-2,3-dihydro-spiro[benzofuran-2(3H),3'-piperidine]hydrochloride, m.p. 240°-241° C.

d.

7-Chloro-2,3-dihydro-1'-[3-(6-fluoro-1,2-benzisoxazol-3-yl)propyl]-spiro[benzofuran-2(3H),3'-piperidine]-maleate In 50 ml dry DMF were combined 3.12 g (11.99 mmol) 7-chloro-2,3-dihydro-spiro[benzofuran-2(3H),3'-piperidine]hydrochloride of Example 9c, 4.00 g (1.25 equivalents, 80% in toluene) 3-(3-chloropropyl)-6-fluoro-1,2-benzoisoxazole of Example 1d, 9.93 g (6 equivalents) milled anhydrous K$_2$CO$_3$, and 0.75 g KI as catalyst. The reaction mixture was heated at 90° C. with stirring under nitrogen for 2 hours then filtered. The filtrate was reduced in vacuo to an oil. The oil was partitioned between 1:1 10% Na$_2$CO$_3$ solution and ether. The ether was separated and washed twice with water, saturated aqueous salt solution, and dried over MgSO$_4$. The ether solution was filtered, then adjusted to pH 1 with ethereal maleic acid. The resultant precipitate was collected and recrystallized from (10:1) ethyl acetate/isopropanol to yield 7-chloro-2,3-dihydro-1'-[3-(6-fluoro-1,2-benzisoxazol-3-yl)propyl]-spiro[benzofuran-2(3H),3'-piperidine]maleate, 2.07 g (33%), m.p. 128° C.

Analysis: Calculated for C$_{22}$H$_{22}$ClFN$_2$O$_2$·C$_4$H$_4$O$_4$: 60.41%C, 5.07%H, 5.42%N. Found: 60.20%C, 5.13%H, 5.33%N.

We claim:

1. A compound having the formula

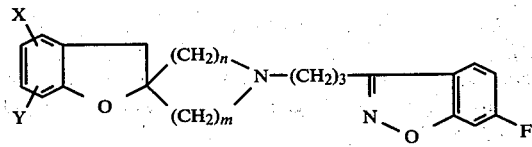

where X and Y are the same or different and are hydrogen, halogen, lower alkoxy, lower alkyl, nitro, hydroxyl, and CF$_3$; and n is an integer of 1 or 2; m is an integer of 2 or 3; and the sum of m and n is 3 or 4; and the pharmaceutically acceptable acid addition salts thereof.

2. The compound as defined in claim 1 which is 2,3-dihydro-1'-[3-(6-fluoro-1,2-benzisoxazol-3-yl)propyl]-spiro[benzofuran-2(3H),4'-piperidine] or a pharmaceutically acceptable salt thereof.

3. The compound as defined in claim 1 which is 5-bromo-2,3-dihydro-1'-[3-(6-fluoro-1,2-benzisoxazol-3-yl)propyl]-spiro[benzofuran-2(3H),4'-piperidine] or a pharmaceutically acceptable salt thereof.

4. The compound as defined in claim 1 which is 5,7-dichloro-2,3-dihydro-1'-[3-(6-fluoro-1,2-benzoisoxazol-3-yl)propyl]-spiro[benzofuran-2(3H),3'-piperidine] or a pharmaceutically acceptable salt thereof.

5. The compound as defined in claim 1 which is 5-chloro-2,3-dihydro-1'-[3-(6-fluoro-1,2-benzisoxazol-3-yl)propyl]-spiro[benzofuran-2(3H),4'-piperidine] or a pharmaceutically acceptable salt thereof.

6. The compound as defined in claim 1 which is 5-bromo-7-chloro-2,3-dihydro-1'-[3-(6-fluoro-1,2-benzisoxazol-3-yl)propyl]-spiro[benzofuran-2(3H),4'-piperidine] or a pharmaceutically acceptable salt thereof.

7. The compound as defined in claim 1 which is 7-chloro-2,3-dihydro-1'-[3-(6-fluoro-1,2-benzisoxazol-3-yl)propyl]-spiro[benzofuran-2(3H),4'-piperidine] or a pharmaceutically acceptable salt thereof.

8. The compound as defined in claim 1 which is (R,S)-2,3-dihydro-1'-[3-(6-fluoro-1,2-benzisoxazol-3-yl)propyl]-spiro[benzofuran-2(3H),3'-piperidine] or a pharmaceutically acceptable salt thereof.

9. The compound as defined in claim 1 which is 5-chloro-2,3-dihydro-1'-[3-(6-fluoro-1,2-benzisoxazol-3-yl)propyl]-spiro[benzofuran-2(3H),3'-piperidine] or a pharmaceutically acceptable salt thereof.

10. The compound as defined in claim 1 which is 7-chloro-2,3-dihydro-1'-[3-(6-fluoro-1,2-benzisoxazol-3-yl)propyl]-spiro[benzofuran-2(3H),3'-piperidine] or a pharmaceutically acceptable salt thereof.

11. A compound as defined in claim 1 wherein X and Y are hydrogen and lower alkoxy.

12. A compound as defined in claim 1 wherein X and Y are the same or different and are hydrogen and lower alkyl.

13. A compound as defined in claim 1 wherein X and Y are the same or different and are hydrogen and hydroxyl.

14. A compound as defined in claim 1 wherein X and Y are the same or different and are hydrogen and CF$_3$.

15. A compound as defined in claim 1 where X and Y are the same or different and are hydrogen and nitro.

16. A hypotensive composition comprising an effective blood pressure reducing amount of a compound having the formula

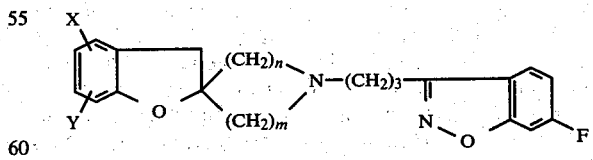

where X and Y are the same or different and are hydrogen, halogen, lower alkoxy, lower alkyl, nitro, hydroxyl and CF$_3$; n is an integer of 1 or 2; m is an integer of 2 or 3; and the sum of m and n is 3 or 4; and the pharmaceutically acceptable acid addition salts thereof.

17. A composition as defined in claim 16 wherein X and Y are selected from hydrogen and halogen.

18. A composition as defined in claim 16 wherein the active ingredient is 2,3-dihydro-1'-[3-(6-fluoro-1,2-benzisoxazol-3-yl)propyl]-spiro[benzofuran-2(3H),4'-piperidine] or a pharmaceutically acceptable salt thereof.

19. A composition as defined in claim 16 wherein the active ingredient is 5-bromo-2,3-dihydro-1'-[3-(6-fluoro-1,2-benzisoxazol-3-yl)propyl]-spiro[benzofuran-2(3H),4'-piperidine] or a pharmaceutically acceptable salt thereof.

20. A composition as defined in claim 16 wherein the active ingredient is 5,7-dichloro-2,3-dihydro-1'-[3-(6-fluoro-1,2-benzisoxazol-3-yl)propyl]-spiro[benzofuran-2(3H),3'-piperidine] or a pharmaceutically acceptable salt thereof.

21. A composition as defined in claim 16 wherein the active ingredient is 5-chloro-2,3-dihydro-1'-[3-(6-fluoro-1,2-benzisoxazol-3-yl)propyl]spiro[benzofuran-2(3H),4'-piperidine] or a pharmaceutically acceptable salt thereof.

22. A composition as defined in claim 16 wherein the active ingredient is 5-bromo-7-chloro-2,3-dihydro-1'-[3-(6-fluoro-1,2-benzisoxazol-3-yl)propyl]-spiro[benzofuran-2(3H),4'-piperidine] or a pharmaceutically acceptable salt thereof.

23. A composition as defined in claim 16 wherein the active ingredient is 7-chloro-2,3-dihydro-1'-[3-(6-fluoro-1,2-benzisoxazol-3-yl)propyl]-spiro[benzofuran-2(3H),4'-piperidine] or a pharmaceutically acceptable salt thereof.

24. A composition as defined in claim 16 wherein the active ingredient is (R,S)-2,3-dihydro-1'-[3-(6-fluoro-1,2-benzisoxazol-3-yl)propyl]-spiro[benzofuran-2(3H),3'-piperidine] or a pharmaceutically acceptable salt thereof.

25. A composition as defined in claim 16 wherein the active ingredient is 5-chloro-2,3-dihydro-1'-[3-(6-fluoro-1,2-benzisoxazol-3-yl)propyl]-spiro[benzofuran-2(3H),3'-piperidine] or a pharmaceutically acceptable salt thereof.

26. A composition as defined in claim 16 wherein the active ingredient is 7-chloro-2,3-dihydro-1'-[3-(6-fluoro-1,2-benzisoxazol-3-yl)propyl]-spiro[benzofuran-2(3H),3'-piperidine] or a pharmaceutically acceptable salt thereof.

27. A method of lowering the blood pressure in a mammal which comprises administering to a mammal a blood pressure reducing amount of a compound of the formula

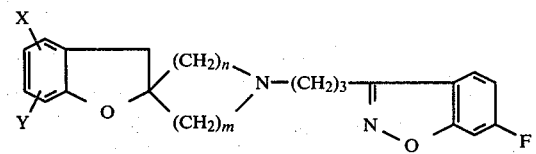

where X and Y are the same or different and are hydrogen, halogen, lower alkoxy, lower alkyl, nitro, hydroxyl and $CF_3$; n is an integer of 1 or 2; m is an integer of 2 or 3; and the sum of m and n is 3 or 4; and the pharmaceutically acceptable acid addition salts thereof.

28. The method as defined in claim 27 wherein X and Y are selected from hydrogen and halogen.

29. A method as defined in claim 27 wherein the active ingredient is 2,3-dihydro-1'-[3-(6-fluoro-1,2-benzisoxazol-3-yl)propyl]-spiro[benzofuran-2(3H),4'-piperidine] or a pharmaceutically acceptable salt thereof.

30. A method as defined in claim 27 wherein the active ingredient is 5-bromo-2,3-dihydro-1'-[3-(6-fluoro-1,2-benzisoxazol-3-yl)propyl]-spiro[benzofuran-2(3H),4'-piperidine] or a pharmaceutically acceptable salt thereof.

31. A method as defined in claim 27 wherein the active ingredient is 5,7-dichloro-2,3-dihydro-1'-[3-(6-fluoro-1,2-benzisoxazol-3-yl)propyl]-spiro[benzofuran-2(3H),3'-piperidine] or a pharmaceutically acceptable salt thereof.

32. A method as defined in claim 27 wherein the active ingredient is 5-chloro-2,3-dihydro-1'-[3-(6-fluoro-1,2-benzisoxazol-3-yl)propyl]-spiro[benzofuran-2(3H),4'-piperidine] or a pharmaceutically acceptable salt thereof.

33. A method as defined in claim 27 wherein the active ingredients is 5-bromo-7-chloro-2,3-dihydro-1'-[3-(6-fluoro-1,2-benzisoxazol-3-yl)propyl]-spiro[benzofuran-2(3H),4'-piperidine] or a pharmaceutically acceptable salt thereof.

34. A method as defined in claim 27 wherein the active ingredient is 7-chloro-2,3-dihydro-1'-[3-(6-fluoro-1,2-benzisoxazol-3-yl)propyl]-spiro[benzofuran-2(3H),4'-piperidine] or a pharmaceutically acceptable salt thereof.

35. A method as defined in claim 27 wherein the active ingredient is (R,S)-2,3-dihydro-1'-[3-(6-fluoro-1,2-benzisoxazol-3-yl)propyl]-spiro[benzofuran-2(3H),3'-piperidine] or a pharmaceutically acceptable salt thereof.

36. A method as defined in claim 27 wherein the active ingredient is 5-chloro-2,3-dihydro-1'-[3-(6-fluoro-1,2-benzisoxazol-3-yl)propyl]-spiro[benzofuran-2(3H),3'-piperidine] or a pharmaceutically acceptable salt thereof.

37. A method as defined in claim 27 wherein the active ingredient is 7-chloro-2,3-dihydro-1'-[3-(6-fluoro-1,2-benzisoxazol-3-yl)propyl]-spiro[benzofuran-2(3H),3'-piperidine] or a pharmaceutically acceptable salt thereof.

* * * * *